US011596459B2

(12) United States Patent
Feng et al.

(10) Patent No.: US 11,596,459 B2
(45) Date of Patent: Mar. 7, 2023

(54) THREAD DESIGN FOR BONE SCREW

(71) Applicant: THE UNIVERSITY OF HONG KONG, Hong Kong (CN)

(72) Inventors: Xiaoreng Feng, Hong Kong (CN); Frankie Ka Li Leung, Hong Kong (CN)

(73) Assignee: THE UNIVERSITY OF HONG KONG, Hong Kong (CN)

(*) Notice: Subject to any disclaimer, the term of this patent is extended or adjusted under 35 U.S.C. 154(b) by 0 days.

(21) Appl. No.: 17/606,987

(22) PCT Filed: May 9, 2020

(86) PCT No.: PCT/CN2020/089350
§ 371 (c)(1),
(2) Date: Oct. 27, 2021

(87) PCT Pub. No.: WO2020/224657
PCT Pub. Date: Nov. 12, 2020

(65) Prior Publication Data
US 2022/0160410 A1 May 26, 2022

Related U.S. Application Data

(60) Provisional application No. 62/845,455, filed on May 9, 2019.

(51) Int. Cl.
*A61B 17/86* (2006.01)
*A61B 17/70* (2006.01)
*A61B 17/04* (2006.01)

(52) U.S. Cl.
CPC ...... *A61B 17/8625* (2013.01); *A61B 17/7001* (2013.01); *A61B 2017/044* (2013.01); *A61B 2017/8655* (2013.01)

(58) Field of Classification Search
CPC ......... A61B 17/8625; A61B 2017/8655; F16B 25/0047
(Continued)

(56) References Cited

U.S. PATENT DOCUMENTS 4,600,224 A * 7/1986 Blose ................. E21B 17/0423
285/333
6,315,564 B1 * 11/2001 Levisman .......... A61B 17/8625
606/315
(Continued)

FOREIGN PATENT DOCUMENTS

| CN | 200998298 Y | 1/2008 |
| CN | 103126758 A | 6/2013 |

(Continued)

OTHER PUBLICATIONS

International Search Report in corresponding PCT Application No. PCT/CN2020/089350, dated Aug. 11, 2020.
(Continued)

*Primary Examiner* — Julianna N Harvey
(74) *Attorney, Agent, or Firm* — Leason Ellis LLP

(57) ABSTRACT

An implant device (100d) for engagement with a bone of a subject, said the implant device (100d) comprising a distal end (102d), a proximal end (104d), a central shaft (106d), a longitudinal central axis (108d) and a helical thread portion (110d) having a leading edge (114d) and a trailing edge (116d). A portion of the leading edge (114d) extends in a direction towards the distal end (102d) of the implant further than the most distal portion of the root (112d) of the thread portion (110d); and wherein the trailing edge (116d) extends in a direction of from the most proximal portion of the root (112d) in a radial outward direction and towards the distal end (102d); and a crest portion (118d) disposed between the leading edge (114d) and the trailing edge (116d) and wherein said the crest portion (118d) forms a radially outward
(Continued)

portion of the thread portion (110*d*). Hence, the implant device (100*d*) improved the axial pull-out strength and reduced stress concentration.

13 Claims, 13 Drawing Sheets

(58) Field of Classification Search
USPC .................................................. 411/411, 423
See application file for complete search history.

(56) References Cited

U.S. PATENT DOCUMENTS

| | | | | |
|---|---|---|---|---|
| 6,386,877 | B1* | 5/2002 | Sutter | A61F 2/4241 |
| | | | | 433/173 |
| 6,572,315 | B1* | 6/2003 | Reed | F16B 39/30 |
| | | | | 411/411 |
| 2002/0136616 | A1* | 9/2002 | Birkelbach | F16B 25/0021 |
| | | | | 411/411 |
| 2003/0067169 | A1* | 4/2003 | Church | F16L 15/06 |
| | | | | 285/390 |
| 2003/0197376 | A1* | 10/2003 | Sivley, IV | E21B 43/106 |
| | | | | 285/333 |
| 2006/0009773 | A1* | 1/2006 | Jackson | F16B 35/047 |
| | | | | 606/301 |
| 2007/0141110 | A1 | 6/2007 | Stone et al. | |
| 2008/0286720 | A1* | 11/2008 | Reed | A61C 8/0074 |
| | | | | 433/174 |
| 2011/0012349 | A1* | 1/2011 | Church | F16L 15/06 |
| | | | | 285/334 |
| 2012/0191208 | A1* | 7/2012 | Olson | A61B 17/8605 |
| | | | | 623/21.18 |
| 2015/0157425 | A1* | 6/2015 | Bar Shalom | A61C 8/0037 |
| | | | | 433/174 |

FOREIGN PATENT DOCUMENTS

| | | |
|---|---|---|
| CN | 104095677 A | 10/2014 |
| CN | 204484286 U | 7/2015 |
| EP | 1656899 A1 | 5/2006 |

OTHER PUBLICATIONS

International Preliminary Report on Patentability in corresponding PCT Application No. PCT/CN2020/089350.

* cited by examiner

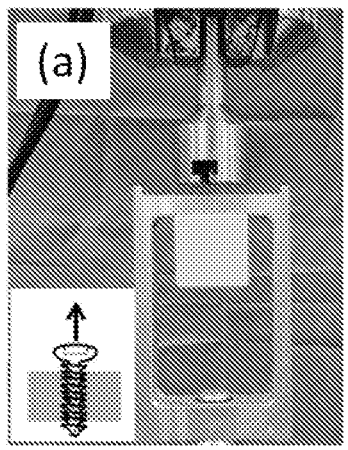
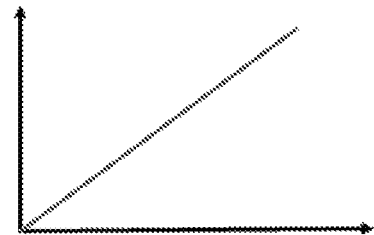
FIG. 7A
FIG. 7B
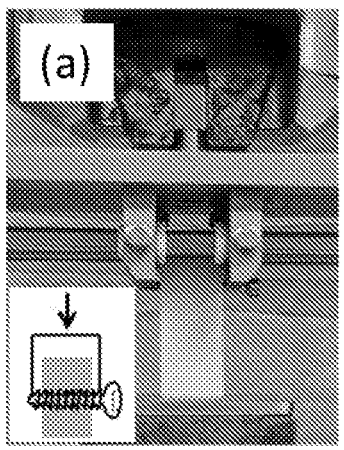
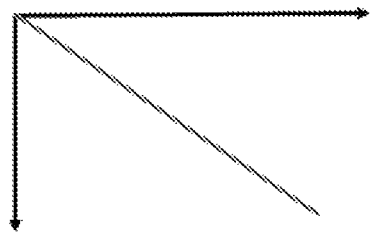
FIG. 8A
FIG. 8B

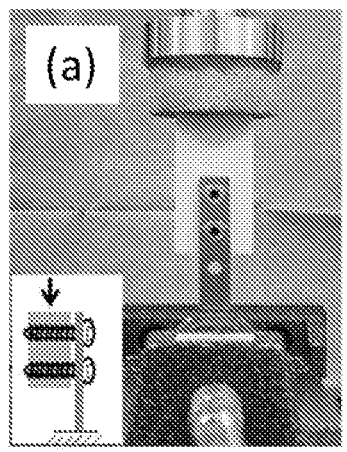
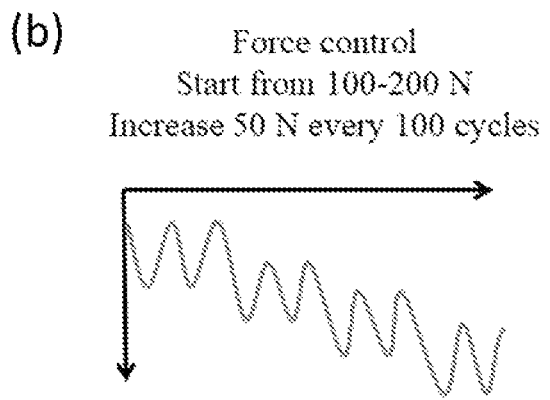
FIG. 9A
FIG. 9B
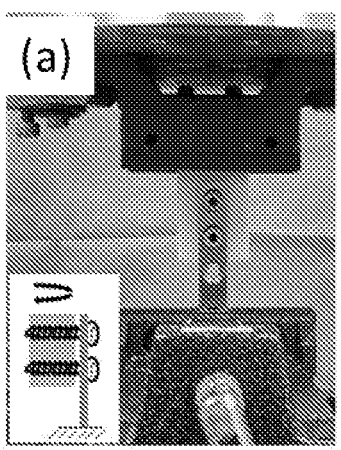
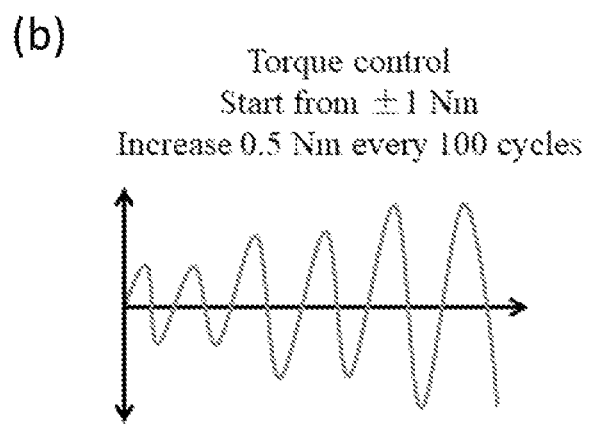
FIG. 10A
FIG. 10B

THREAD DESIGN FOR BONE SCREW

CROSS-REFERENCE TO RELATED PATENT APPLICATIONS

This application is a U.S. National Phase Application under 35 U.S.C. § 371 of International Patent Application No. PCT/CN2020/089350, filed May 9, 2020, and claims the benefit of priority under 35 U.S.C. Section 119(e) of U.S. Application No. 62/845,455, filed May 9, 2019, all of which are incorporated by reference in their entireties. The International Application was published on Nov. 12, 2020 as International Publication No. WO 2020/224657 A1.

TECHNICAL FIELD

The present invention relates to a bone implant device for engagement with bone tissue. More particularly, the present invention provides a bone implant device for reducing loosening thereof in bone tissue.

BACKGROUND OF THE INVENTION

Bone implant devices are typically used for fixation and engagement with typically include a threaded engagement portion for engagement with and fixation within bone material.

Such bone implant devices have numerous applications in the field of orthopaedics and orthopaedic surgery, such as when used alone to reduce a fracture or secure fractured bone for example, to secure and fix other fracture or trauma hardware, such as fracture plate, or secure implants such as protheses in the field of arthroplasty.

As is known, other bone implant devices, which include a threaded engagement portion for engagement with and fixation in bone, include devices such as pedicle screws, suture anchors and other fixation type devices.

Also as is known within the art of bone implant devices and fastener and fixation type devices, including those recited above, which typically include a threaded portion for engagement with bone tissue, there exist numerous problems associated with the biomechanical and biological properties of bone and physiological response of bone in response to the presence of such devices and the loading to bone.

These may potentially reduce the integrity of engagement and fixation in bone, and securement of such devices within bone.

By way of example, bone fasteners such as bone screws, bone nails, and bone plates may have the effect of weakening or compromising the integrity of surrounding tissue through a physiological mechanism, which is known as stress shielding, which results from bone adjacent a fixation element or implant resorbing due to the absence of localised loading.

Due to such localised changes in bone tissue adjacent a fixation element, fastener or implant can further result in compromise of a mechanical engagement device and fixation, by a further mechanism known termed aseptic loosening, whereby the fit and engagement between orthopeadic implants and bone tissue is compromised resulting in a device loosening over time.

Accordingly, this may further cause loosening and even catastrophic failure of the mechanical system or the device, which may be exacerbated by the device crushing and compacting adjacent bone tissue in some cases.

Also, further problems which may result include what is known as progressive "cut out", in which a device may progressively penetrate through the bone from relative movement between the device and bone, until the device breaks through the cortex entirely.

As is known, such biomechanical problems associated with such devices are often related to and can be exacerbated by biological changes due to the processes of bone generation and bone remodelling.

As is also known, a common biological change in bone is the loss of bone mass and structural strength due to imbalance in the bone remodelling process, a condition known as osteopenia, or its more extreme form the progression to osteoporosis.

Global life expectancies of people have risen during the 21st century, and an increasing number of otherwise healthy and able-bodied elderly people suffer from painful and debilitating fractures due to osteoporosis.

Fractures of the hip, shoulder and spine of a subject are especially prevalent due to the relatively high content of cancellous, or "spongy," tissue within the larger, load-bearing bones.

It has been shown that in individuals suffering from osteoporosis, these bones often develop numerous cavities and cysts within the spongy bone tissue of a subject, that can compromise structural strength and lead to higher fracture and rates.

In the field of orthopaedics, a common form of treatment of patients for such fractures is surgical fixation by way of the implantation of metal rods or screws that are used to secure bone fragments in their original or appropriate anatomical positions, during the healing process.

Within the human body, all bone tissue, particularly bone tissue already weakened by conditions such as osteoporosis, degenerative disorders, compromised bone stock, is susceptible to complications caused by the migration and loosening of medical devices including implants, fixation devices and bone anchors.

Migration of a device within bone tissue can cause instability at fracture sites, aseptic loosening of implants, increased stresses on implants and fixation devices and associated hardware, all of which may cause fatigue and failure, and in the case of bone anchors this may cause instability and potential loosening and pull-out and other complications, all of which reduce overall musculoskeletal health and integrity of bone tissue and bone stability.

As is known, the presence of a device within bone stock of a subject may contribute to or may cause weakening of the bone through mechanisms such as bone resorption due to stress shielding.

OBJECT OF THE INVENTION

It is an object of the present invention to provide an implant device which overcome or at least partly ameliorate at least some deficiencies as associated with the prior art.

SUMMARY OF THE INVENTION

In a first aspect, the present invention provides an implant device for engagement with a bone of a subject, said implant device comprising a distal end, a proximal end, a central shaft extending therebetween and a longitudinal central axis;
  said implant device further including a helical thread portion extending circumferentially about said central shaft and extending in a direction of from the distal end of the implant device and towards the proximal end thereof, and a root at the base of the helical thread portion adjacent the central shaft of the of the implant device, said helical thread portion including:

a leading edge and a trailing edge, both of which extend at least radially outwardly from the central shaft and define the thread portion therebetween, whereby the root of the thread portion is defined therebetween in a direction of the longitudinal central axis of the implant device;

wherein said leading edge faces in a direction of at least towards the distal end of the implant device, and wherein said trailing edge faces at least in a direction of towards the proximal end of the implant device;

wherein a portion of the leading edge extends in a direction towards the distal end of the implant further than the most distal portion of the root of the thread portion and wherein the distance in the longitudinal direction from the most proximal portion of the root to the most distal portion of the leading edge is greater than the longitudinal length of the root, and such that said portion of the leading edge forms a recess between the central shaft and the leading edge, wherein the portion of said leading edge defining said recess between the central shaft and the leading edge provides for abutment and engagement with bone tissue of a subject disposed within said recess; and wherein the trailing edge extends in a direction of from the most proximal portion of the root in a radial outward direction and towards the distal end; and a crest portion disposed between the leading edge and the trailing edge and wherein said crest portion forms a radially outward portion of the thread portion, and wherein, wherein the crest portion provides an engagement surface for abutment and engagement with bone of a subject radially disposed from said thread portion.

The crest has a surface may substantially planar and parallel with the longitudinal central axis of the implant device which provides said engagement surface, or may be an outwardly curved outer surface which provides said engagement surface. The crest may form at least a portion of the trailing edge.

The recess formed by the leading edge is sized and shaped, such that upon engagement with radially disposed bone adjacent the thread portion, provides for distribution of stress induced in said bone adjacent the leading edge and provides for reducing stress concentration in bone adjacent said leading edge.

The engagement surface of said crest portion, upon engagement with radially disposed bone adjacent the thread portion, provides for distribution of stress induced in said bone adjacent the crest portion along said engagement surface, and said engagement surface provides for reducing stress concentration in bone adjacent said crest portion.

The crest portion may have a greater longitudinal length than that of the root portion in the direction of the longitudinal central axis of the implant device.

The leading edge of the thread portion may include a first facet for abutment and engagement with bone tissue of a subject.

The first facet may have a substantially planar surface and extends substantially radially outwardly from the distal side of the root portion at the central shaft and extends towards the crest portion and an inclination angle in the range of from 95 degrees and 150 degrees subtended between said planar surface and the longitudinal central axis. The inclination angle may be in a range of from 100 degrees and 130 degrees subtended between said planar surface and the longitudinal central axis. The inclination angle may be about 120 degrees subtended between said planar surface and the longitudinal central axis.

The leading edge further may further include a second facet, wherein second facet is disposed between the root of the thread and the first facet and has a substantially planar surface.

The second facet may extend radially outwardly towards the first facet, and wherein said second facet extends from the shaft substantially normal to the longitudinal central axis of the implant device.

The trailing edge of thread portion may include a third facet for abutment and engagement with bone tissue of a subject, wherein the third facet is substantially planar and extends from the proximal side of the root portion at the central shaft and extends towards the crest portion at an inclination to the central shaft.

The engagement surface of the crest portion may be at least partially provided by the leading edge, and the engagement surface of the crest portion may be at least partially provided by the trailing edge.

The recess is sized and shaped such that upon the implant device and adjacent bone in which the device is embedded being urged towards each other on a first side of the implant, at least a portion of the leading edge of the thread portion is urged against bone disposed within the recesses on the opposed side of the implant device.

The thread portion may have a constant cross-sectional area and geometry, or the thread portion may have a varying cross-sectional area and geometry.

The thread portion may have a constant thread pitch, or the thread portion may have a varying a constant thread pitch.

The implant device may be formed from a metal or metal alloy material. The metal or metal alloy material may be selected from the group including stainless steel, titanium, titanium alloy, cobalt-chromium alloy or the like.

The implant device may be formed from a polymeric material or polymer-based material. The polymeric material or polymer-based material may be polyether ether ketone (PEEK).

The implant device may be a bone screw, an orthopaedic locking screw, a pedicle screw device, the femoral head engagement element of a dynamic hip screw, a bone suture anchor, or an orthopaedic implant prosthesis device.

In a second aspect, the present invention provides a kit comprising one or more implant devices according to the first aspect The one or more implant devices may be a bone screw. The kit may comprise one or more fracture fixation devices.

In a third aspect, the present invention provides a system for fixing a first portion of bone relative to a second portion of bone, said system having 2 or more implant devices according to the first aspect and a bridging member, wherein a first implant device is engageable with the first portion of bone and a second implant device is engageable with the second portion of bone, wherein the distal ends of the implant devices are engageable with said portions of bone and the proximal ends are engageable with said bridging member.

The one or more implant devices are pedicle screws and the bridging member may be a rod, and the system is a spinal fusion system. The rod may be adjustable so as to provide adjustable movement of the first portion of bone and the second portion of bone relative to each other. The system may be a trauma fixation system.

BRIEF DESCRIPTION OF THE DRAWINGS

In order that a more precise understanding of the above-recited invention can be obtained, a more particular description of the invention briefly described above will be rendered by reference to specific embodiments thereof that are illustrated in the appended drawings.

The drawings presented herein may not be drawn to scale and any reference to dimensions in the drawings or the following description is specific to the embodiments disclosed.

FIG. 1A shows an enlarged sectional side view of a portion of the Prior Art bone screw of FIG. 1A;

FIG. 7A is a diagram showing the experimental setup of assessing the displacement of a comparison between two bone screws shown of FIG. 3B and FIG. 3D in response to a pulling force;

FIG. 7B is a graphical representation of the applied displacement control utilised the experiment described in FIG. 7A;

FIG. 8A is a diagram showing an experimental setup of assessing the displacement of a comparison between two bone screws shown of FIG. 3B and FIG. 3D in response to a pushing force;

FIG. 8B is a graphical representation of the applied displacement control utilised in the experiment described in FIG. 8A;

FIG. 9A is a diagram showing an experiment setup of assessing the displacement of a comparison between two bone screws shown of FIG. 3B and FIG. 3D in response to a craniocaudal force;

FIG. 9B is a graphical representation of the applied force control utilised in the experiment described in FIG. 9A;

FIG. 10A is a diagram showing an experiment setup of assessing the displacement of a comparison between two bone screws shown of FIG. 3B and FIG. 3D in response to a torsional force;

FIG. 10B is a graphical representation of the applied torque control utilised in the experiment described in FIG. 10A;

DETAILED DESCRIPTION OF THE DRAWINGS

Figure 1A:
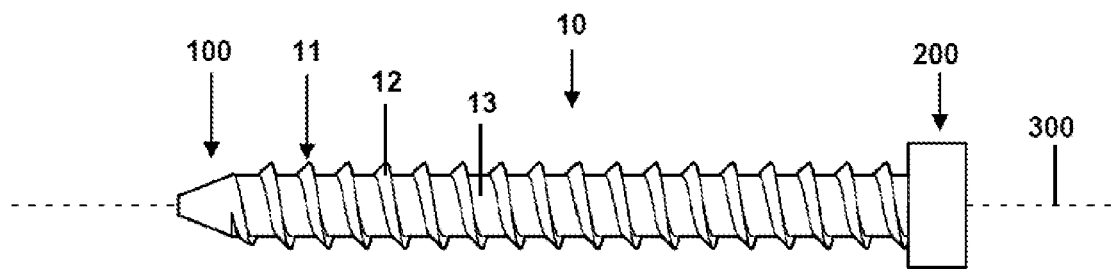
FIG. 1A[MCG1] shows a side view of an exemplary bone screw according to the Prior Art.

The present inventors have identified shortcomings in bone implant devices of the prior art, and upon identification of the problems with the prior art, have provided a bone implant device which overcomes the problems of the prior art.

BACKGROUND EXPLANATION OF PRESENT INVENTION

The present invention is a new thread design useful in improving the safety and efficacy of orthopaedic bone screws, and other orthopaedic implant devices.

The novel thread design of the present invention achieves this outcome by reducing the formation of stress concentration zones within in the bone tissue surrounding the screw.

The present invention may be used to improve safety and efficacy for all kinds of bone screws, particularly traditional compression, locking and pedicle screws—the three most commonly-used screws in orthopaedic surgery today.

The present generations of bone screws and fixation elements have been found to become loosened too easily after surgical implantation, often when the patient's body weight is applied to a previously broken bone for example.

As has been noted by the present inventors, screw loosening is a very common form of bone screw fixation failure, with a failure rate of up to 20% that has been shown to increase in severity with patient age.

Overloading of the bone tissue has been identified by the present inventors as the main factor contributing to screw loosening and aseptic loosening of bone implant devices. This has been found to occur when the shape and/or geometry of the screw, in particular the screw thread profile of the screw, causes areas of excessive stress concentration to form in the surrounding bone tissue.

As has been shown, excessive stress concentration can damage bone tissue, leading to bone to be reabsorbed by cells within the body. If too much bone tissue is reabsorbed around or adjacent a screw, the screw will typically become loose, and may lead to failure of the screw to stay in the proper position within the bone, or in some cases deformation and even fracture of the screw.

As has been identified by the present inventors, an implant device of the bone screw type having a buttress thread, provides several biomechanical disadvantages:
 (i) Excessive bone loading at portions of bone adjacent thread portions on a first side of the implant device,
 (ii) Insufficient loading of bone to the second side of the implant device, and
 (iii) Separation at the bone—implant interface of the second side of the implant device.

Excessive localised bone loading can cause localised bone damage from crushing of bone material.

Stress shielding due to insufficient bone loading results in bone resorption due to a mechanobiological effect on bone.

Collectively and individually, both excessive and insufficient loading to bone adjacent can exacerbate detrimental effects on surrounding bone tissue, resulting in;
 Aseptic loosening,
 Implant migration through bone,
 Failure of an implant/bone fixation or maintenance system.
 Catastrophic failure of bone material and implant devices.

This can lead to undesirable bone loss in bone tissue, causing aseptic implant loosening through the resorption of bone material by a mechanobiological effect of stress shielding and associated complaints as discussed above.

Whilst the FEA model utilised to provide the above observed phenomena is directed to a single static loading, as is known by those skilled in the art, FEA modelling is a useful analytical tool for biomechanical systems, implant and bone.

The observed deficiencies of such a fixation device having a buttress thread which is commonly used within the field of orthopaedics as identified by the present inventors is considered demonstrative of the clinical bone/implant environment.

Introduction of the Present Invention

As noted by the present inventors, previously, engineers designing bone screw threads and orthopaedic implants, have generally considered bone as an inert, mechanical substrate, rather than paying sufficient attention to the mechanical properties of its biological activity.

The present inventors have noted that screw threads of implant devices are particularly relevant to load concentrations that are formed when bone tissue is pushed or urged against the side of the screw, which is very common in applications such as spinal implants.

The present invention seeks to incorporate a better understanding of the mechanobiology of bone into screw thread design for bone implant devices, by preventing or at least ameliorating the formation of areas of excessive load and stress in the bone tissue around and adjacent a screw or implant.

The present inventors address problems of the prior art by presenting an innovative, bone stress-reducing bone screw thread design.

The present invention relates to a novel screw thread design applicable to the orthopaedic discipline, which can be incorporated into various implant-type devices for providing a new product.

The novel and inventive aspects of the present invention pertain element relates to a screw thread design utilizing an innovative "reverse undercut barb" shape as described with reference to FIG. 1D onward which provides improved the axial pull-out strength, as well as provides for lateral migration resistance of an implant device embodying the screw thread of the present invention. Included as disclosed are comparison of screw-type devices which embody the thread of the present invention with typical and standard buttress-thread screw devices, for comparative and illustrative purposes.

Figure 1B:
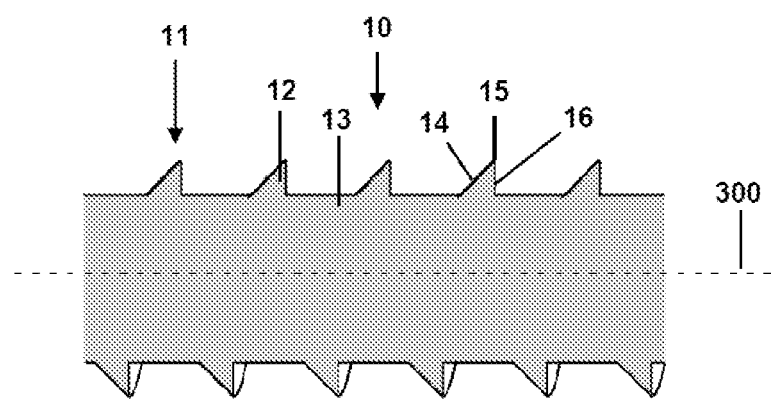
FIG. 1C show a side view of the bone screw of the Prior Art of FIG. 1A and FIG. 1B.
FIG. 1D shows a side view of a portion exemplary first embodiment a screw thread of an implant device according to the present invention.
FIG. 1E shows a side view of a portion exemplary second embodiment a screw thread of an implant device according to the present invention.
Figure 1C:
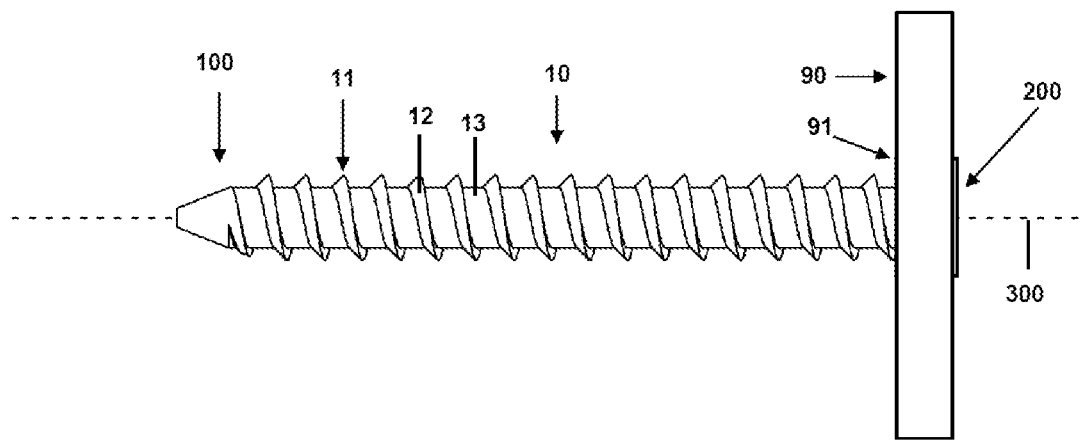

Referring to FIG. 1A, FIG. 1B and FIG. 1C, are a typical orthopaedic buttress screw implant device 10 which is a bone screw of the Prior Art used for fixing fractured or fragmented bone so that fragmented or fractured bone may be reduced to their correct anatomical positions while osteosynthesis, or bone healing, takes place.

As shown in FIG. 1B, the implant device 10 includes a distal end 100 for insertion into bone tissue, and a proximal end 200 that is operated or manipulated by a surgeon, and a central longitudinal axis 300 that extends from proximal to distal direction. The implant device 10 further includes a thread portion 12 comprised of a helical thread 11 having a buttress profile that follows a helical path around central shaft 13 of the implant device 10.

The implant device 10 may be formed from a biocompatible and corrosion-resistant metal alloy, preferably stainless steel, titanium or cobalt-chromium alloy. The implant device 10 may alternatively be formed from a biocompatible rigid or semi-rigid polymeric material suitable for orthopaedic implants and applications, such as polyether ether ketone (PEEK)

Further, the implant device 10 may also be formed from a biocompatible rigid or semi-rigid ceramic material suitable for orthopaedic implants, such as silica or hydroxyapatite-based ceramic materials.

Referring to FIG. 1B, there is shown a sectional view of a portion of the implant device 10. The thread portion 12 includes a proximal facet 16, a crest 15, and a distal facet 14.

The proximal end 200 of implant device 10 may be permanently or removably attached to a further device 90 such as bone plate, intramedullary nail, or other member, which may possess one or more holes 91 extending therethrough.

As is shown in FIG. 1C, the implant device 10 may be attached to the fixation device 90 by first passing the distal end 100 of the implant device 10 through one such hole 91 and advancing the implant device 10 into bone tissue 17 until the proximal end 200 engages with the further device 90, such as through threads or sloped surfaces on end 200 that mate with matching threads or sloped surfaces on hole 91.

Figure 1D:
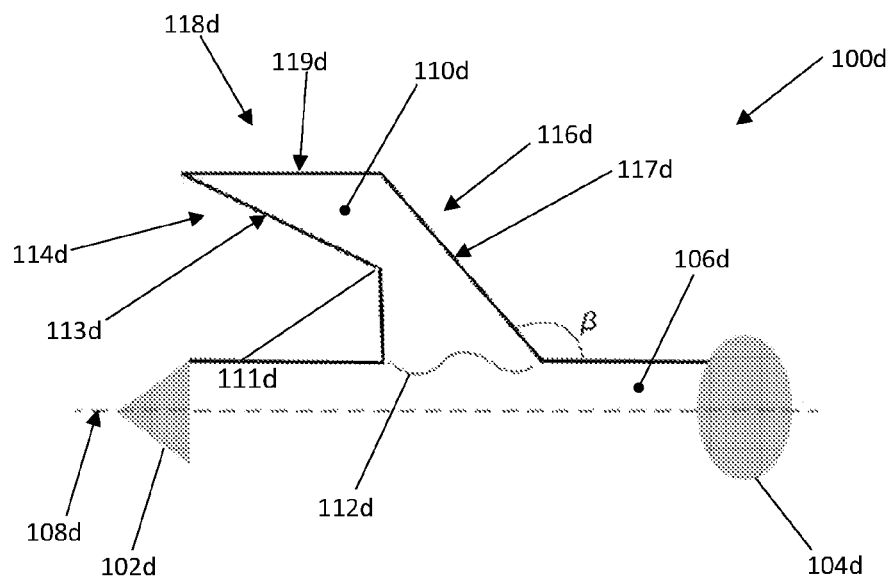

Referring to FIG. 1D, there is show a side view of a portion exemplary first embodiment a screw thread of an implant device 100*d* according to the present invention; As is shown, the implant device 100*d* of the present invention, is for engagement with a bone of a subject.

The implant device 100*d* comprises a distal end 102*d* or "tip", a proximal end 104*d* or "head", a central shaft 106*d* extending between the distal end 102*d* or "tip" and the proximal end 104*d* or "head, and has a longitudinal central axis 108*d*

The implant device 100*d* further includes a helical thread portion 110*d* extending circumferentially about the central shaft 106*d* and extending in a direction of from the distal end 102*d* of the implant device 100*d* and towards the proximal end 104*d* thereof, and a root 112*d* at the base of the helical thread portion 110*d* adjacent the central shaft 106*d* of the of the implant device 100*d*.

The helical thread portion 110*d* is characterized as follows:
there is a leading edge 114*d* and a trailing edge 116*d* which are portions of the thread surface, both of which extend at least radially outwardly from the central shaft 106*d* and define the thread portion 110*d* therebetween
the root 112*d* of the thread portion 110*d* is defined therebetween in a direction of the longitudinal central axis 108*d* of the implant device 100*d*
the leading edge 114*d* faces in a direction of at least towards the distal end 108*d* of the implant device 100*d*, the trailing edge 116*d* faces at least in a direction of towards the proximal end 104*d* of the implant device 100*d*;
a portion of the leading edge 114*d* extends in a direction towards the distal end 108*d* of the implant device 100*d* further than the most distal portion of the root 112*d* of the thread portion 110*d*, so as to form an "undercut structure" facing the distal end 108*d* or "tip"

As will be understood, the distance in the longitudinal direction from the most proximal portion of the root 112*d* to the most distal portion of the leading edge 114*d* is greater than the longitudinal length of the root 112*d*, and such that said portion of the leading edge 114*d* forms a recess or "undercut structure" between the central shaft 106*d* and the leading edge 114*d*.

The portion of the leading edge 114*d* defining the recess between the central shaft and the leading edge 114*d* provides for abutment and engagement with bone tissue of a subject disposed within the recess.

The thread portion 110*d* further includes a crest portion 118*d* disposed between the leading edge 102*d* and the trailing edge 104*d* and wherein the crest portion 118*d* forms a radially outward portion of the thread portion 110*d*, and wherein the crest portion 118*d* provides an engagement surface 119*d* for abutment and engagement with bone of a subject radially disposed from the thread portion 110*d*.

In the present embodiment, the leading edge 114*d* of the thread portion 110*d* includes a first facet 113*d* for abutment and engagement with bone tissue of a subject. The first facet 113*d* has a substantially planar surface and extends substantially radially outwardly from the distal side of the root portion at the central shaft 106*d* and extends towards the crest portion 118*d*.

The first facet 113*d* as shown has a substantially planar surface and extends substantially radially outwardly from the distal side of the root portion 112*d* at the central shaft 106*d* and extends towards the crest portion 118*d* and an inclination angle in the range of from 95 degrees and 165 degrees subtended between the planar surface of the first facet 113*d* and the longitudinal central axis 108*d*.

In other embodiments, the inclination angle may be in a range of from 100 degrees and 130 degrees, or about 120 degrees As is also shown, the leading edge 114*d* further includes a second facet 111*d*, wherein second facet 114*d* is disposed between the root 112*d* of the thread portion 110*d*, and the first facet 113*d*, and has a substantially planar surface.

In the present embodiment, the second facet 111*d* extends radially outwardly towards the first facet 113, and wherein the second facet 111*d* extends from the shaft portion 106*d* substantially normal to the longitudinal central axis 108 of the implant device 100*d*.

As will be understood, the recess or "undercut as provided by the leading edge 114*d* is in the present embodiment, is provided by the first facet 113*d* and the second facet 111*d*.

However as will be appreciated by those skilled in the art, in other or alternate embodiments, the recess may be provided due to the leading edge having one, two, three or more facets, or one facet, and the facets need not necessarily be flat but may be curved in other embodiments.

The trailing edge 116*d* extends in a direction of from the most proximal portion of the root 112*d* in a radial outward direction and towards the distal end 108*d*. The trailing edge 116*d* is provided by a facet surface 117*d* in the present embodiment, which has an angle β larger than 90 degrees with the longitudinal axis 108*d* of the implant device 100*d*.

In the embodiment as is shown in FIG. 1D, the screw thread design of the present invention has three important features. The first feature is that the thread surface a facing the proximal end or "screw head" has an angle larger than 90 degree with the longitudinal axis 108 screw shaft. The second feature is having a flat thread edge 119*d* as a crest portion 118*d*. The third feature is having an undercut structure facing the distal end or "screw tip".

Such features of the present invention provide for an implant device bone tissue which overcome or at least ameliorate problems with the prior art as identified by the present inventors and as discussed above.

It should be noted that:
(i) the recess formed by the leading edge 114*d* is sized and shaped, such that upon engagement with radially disposed bone adjacent the thread portion 119*d*, the recess provides for distribution of stress induced in said bone adjacent the leading edge 114*d* and provides for reducing stress concentration in bone adjacent said leading edge.
(ii) the engagement surface 119*d* of said crest portion 118*d*, upon engagement with radially disposed bone adjacent the thread portion 110*d*, provides for distribution of stress induced in said bone adjacent the crest portion 118*d* along said engagement surface 119*d*, and the engagement surface 119*d* provides for reducing stress concentration in bone adjacent said crest portion.

As will be understood, in embodiments of the invention, the crest portion 118*d* can have a greater longitudinal length than that of the root portion 112*d* in the direction of the longitudinal central axis 108*d* of the implant device 100*d*.

The above provides for assistance in reduction in stress concentration, which as discussed above contributes to the integrity of fixation of an implant in bone tissue, and also reduces, loosening, migration, and failure, by maintaining appropriate loading to one adjacent an implant which reduces stress shielding and adverse bone remodelling.

Also as identified by the present inventors, traditional buttress threads as used in orthopaedic implants can often loosen easily, as such a thread is not designed specifically for human bone.

Accordingly, when the patient or subject provides weight bearing on such a screw with buttress thread design, extremely high stress has been found by the present inventors which will concentrate on the weight bearing part of bone, while no stress occur at the opposite part of bone, both of which can cause bone loss and resorption around the screw.

The recess as provided by the present invention is sized and shaped such that upon the implant device and adjacent bone in which the device is embedded being urged towards each other on a first side of the implant, at least a portion of the leading edge of the thread portion is urged against bone disposed within the recesses on the opposed side of the implant device.

As such, the present invention can provide for a reduction of excess stress on one side of an implant device adjacent the thread portion which reduces bone loss, whilst providing for loading to bone tissue to the thread on the opposed side of the implant device, thus reducing stress shielding and consequential bone loss.

Figure 1E:
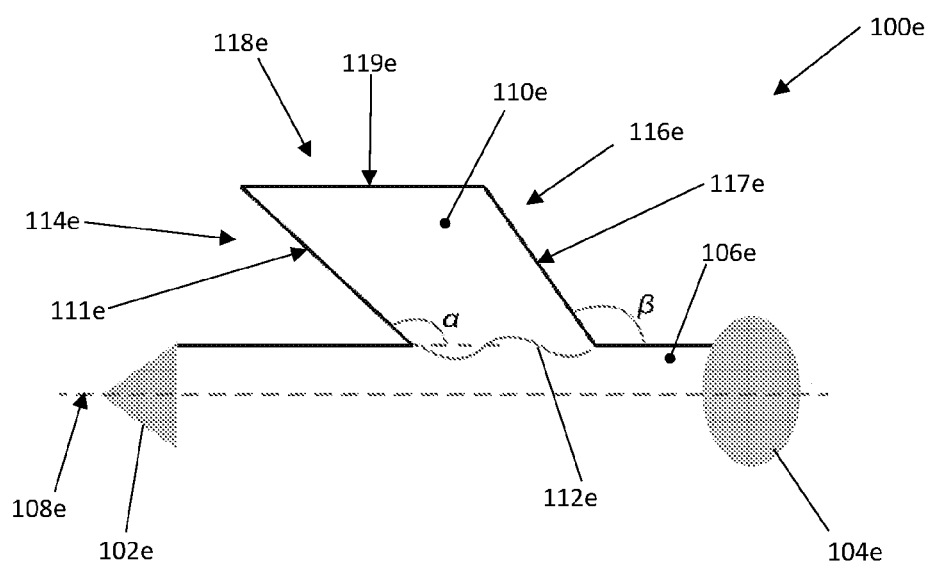

As will be understood by those skilled in the art, an implant device embodying a screw thread as described is applicable to numerous orthopaedic related applications, such applications may include at least a bone screw, an orthopaedic locking screw, a pedicle screw device, the femoral head engagement element of a dynamic hip screw, a bone suture anchor, or an orthopaedic implant prosthesis device, for example. Referring now to FIG. 1E, there is shows a side view of a portion exemplary second embodiment a screw thread of an implant device 100e according to the present invention.

In the present embodiment, the features of the implant device 100e are generally equivalent to those in FIG. 1D, and again the implant device 100e comprises a distal end 102e, a proximal end 104e, a central shaft 106e extending between the distal end 102e and the proximal end 104e, and has a longitudinal central axis 108d The implant device 100e further includes a helical thread portion 110e extending circumferentially about the central shaft 106e and extending in a direction of from the distal end 102e of the implant device 100e and towards the proximal end 104e thereof, and a root 112e at the base of the helical thread portion 110e adjacent the central shaft 106e of the of the implant device 100e.

Similarly, as described with reference to FIG. 1D, the helical thread portion 110e is characterized as follows:
(i) there is a leading edge 114e and a trailing edge 116e which are portions of the thread surface, both of which extend at least radially outwardly from the central shaft 106e and define the thread portion 110e therebetween,
(ii) the root 112e of the thread portion 110e is defined therebetween in a direction of the longitudinal central axis 108e of the implant device 100e,
(iii) the leading edge 114e faces in a direction of at least towards the distal end 108e of the implant device 100e, the trailing edge 116e faces at least in a direction of towards the proximal end 104e of the implant device 100e; and
(iv) a portion of the leading edge 114e extends in a direction towards the distal end 108e of the implant device 100e further than the most distal portion of the root 112e of the thread portion 110e, so as to form an "undercut structure" facing the distal end 108e.
(v) the thread portion 110e further includes a crest portion 118e disposed between the leading edge 102e and the trailing edge 104e and wherein the crest portion 118e forms a radially outward portion of the thread portion 110e, and wherein the crest portion 118e provides an engagement surface 119e for abutment and engagement with bone of a subject radially disposed from the thread portion 110e.

Again, it should be noted that:
(i) the recess formed by the leading edge 114e is sized and shaped, such that upon engagement with radially disposed bone adjacent the thread portion 119e, the recess provides for distribution of stress induced in said bone adjacent the leading edge 114e and provides for reducing stress concentration in bone adjacent said leading edge,
(ii) the engagement surface 119e of said crest portion 118e, upon engagement with radially disposed bone adjacent the thread portion 110e, provides for distribution of stress induced in said bone adjacent the crest portion 118e along said engagement surface 119e, and the engagement surface 119e provides for reducing stress concentration in bone adjacent said crest portion, and
(iii) the recess as provided by the present invention is sized and shaped such that upon the implant device 100e and adjacent bone in which the device is embedded being urged towards each other on a first side of the implant device 100e, at least a portion of the leading edge 114e of the thread portion 110e is urged against bone disposed within the recesses on the opposed side of the implant device 100e.

In the present embodiment, the leading edge 114e is comprised of a single facet 111e, which has a substantially planar surface and extends substantially radially outwardly from the distal side of the root portion 112e at the central shaft 106e and extends towards the crest portion 118e.

Figure 2A:
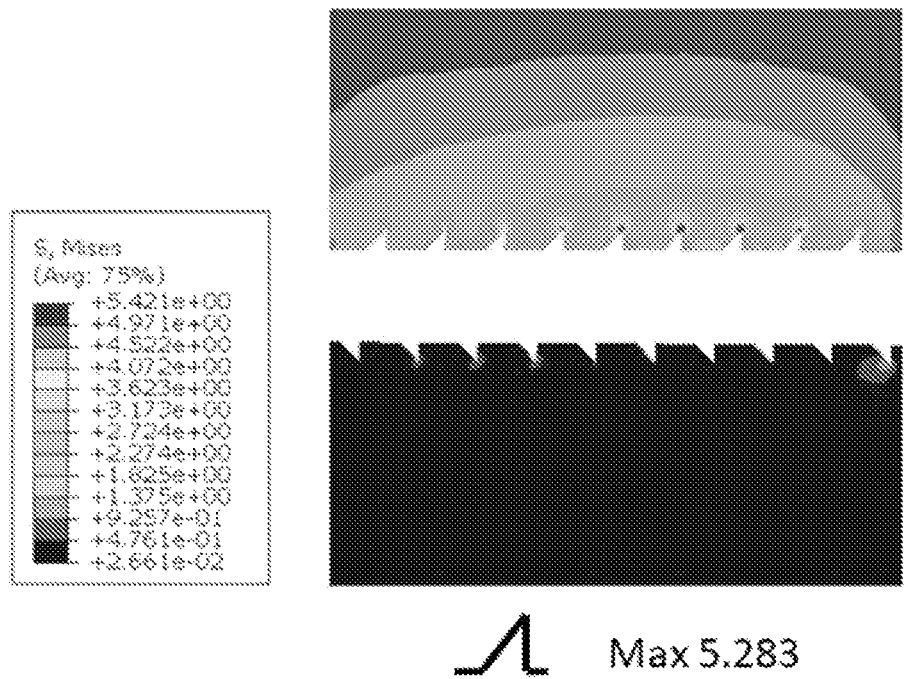
FIG. 2A is graphical representation of the Von Mises stresses induced in the bone material adjacent to a bone screw of the prior art with a typical buttress thread.
Figure 2B:
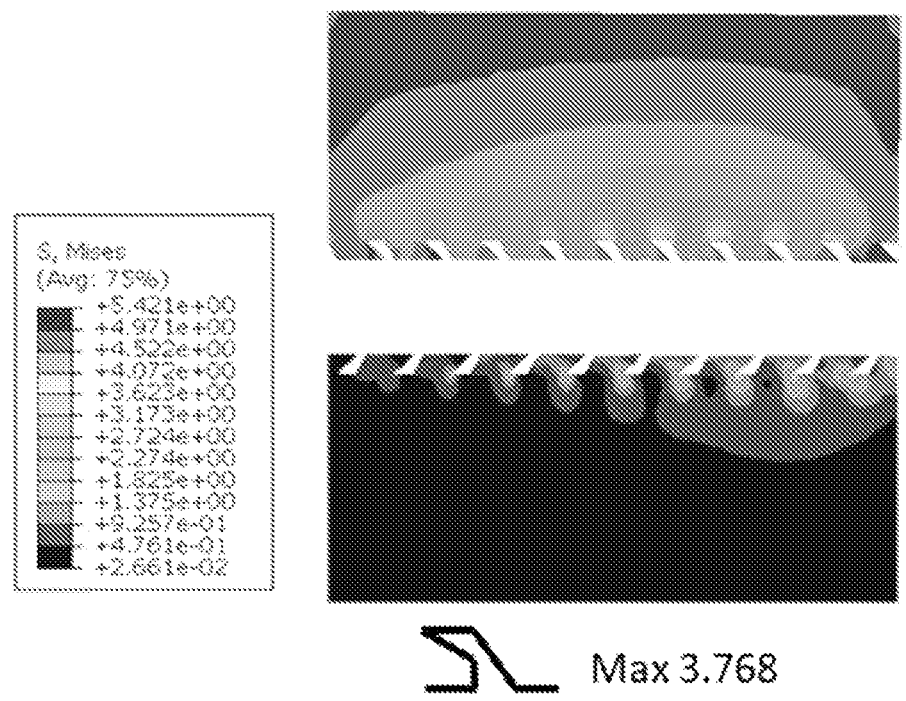
FIG. 2B is a graphical representation of the Von Mises stresses induced in the bone material adjacent to a bone screw with the thread design of FIG. 1D according to the present invention.

The facet 111e as shown has a substantially planar surface and extends substantially radially outwardly from the distal side of the root portion 112e at the central shaft 106e and extends towards the crest portion 118e and an inclination angle in the range of from 95 degrees and 165 degrees (angle α) subtended between the planar surface of the facet 111e and the longitudinal central axis 108e. In other embodiments, the inclination angle may be in a range of from 100 degrees and 130 degrees, or about 120 degrees The trailing edge 116e extends in a direction of from the most proximal portion of the root 112e in a radial outward direction and towards the distal end 108e. The trailing edge 116e is provided by a facet surface 117e in the present embodiment, which has an angle β larger than 90 degrees with the longitudinal axis 108e of the implant device 100e. FIG. 2A and FIG. 2B show the analysis results of the FEA model when a bone screw, with either the buttress thread as shown in FIG. 1B or the undercut thread of FIG. 1D, is inserted into the bone material with a load of 250N applied thereto.

The FEA simulation includes the model implant device of the type used for fixing fractured or fragmented bone so that fragmented or fractured bone may be reduced in their correct anatomical positions while osteosynthesis, or healing, takes place.

The FEA simulation was conducted using the software ABAQUS (6.13/CAE, Simulia, Providence, USA). The simulated implant material utilised was stainless steel with a Young's Modulus of 200 GPa and a Poisson's Ratio of 0.3 applied. The simulated bone tissue was that representative of healthy human trabecular bone with a Young's Modulus of 260 MPa and a Poisson's Ratio of 0.29 applied.

FIG. 2A shows the Von Mises stresses induced in the bone material adjacent the bone screw with typical buttress thread. As is shown in FIG. 2A, upon being urged by the load, the region of the simulated bone tissue, adjacent to the side of the implant that is predominantly facing the direction from which the simulated load originates, is compressed against an adjacent portion of the modelled thread portion and central shaft. Being so compressed, stress concentrations are shown with magnitudes in the simulated bone tissue portions, of a maximum of magnitude of 5.283 MPa.

The stress induced in the bone material of the opposite side, the side that is not facing the direction from which the simulated load originates, is however very small which is almost negligible.

It is noted that both the high stress concentrating on the weight bearing part of bone, and the absence of stress at the opposite part of bone may cause bone loss and resorption around the screw, which precipitates the abovementioned problems of bone stock loss, loss of implant support, aseptic loosening, implant migration, excessive stresses causing bone failure, implant failure, fixation system losing integrity, resulting often in both mechanical clinical complications.

Referring now to FIG. 2B, which depicts modelling of a bone screw in accordance with the present invention, which shows the Von Mises stresses induced in the bone material adjacent the bone screw with the undercut thread of the present invention.

As can be seen, similarly to FIG. 2A, upon being urged by the load, the region of the simulated bone tissue, adjacent to the side of the implant that is predominantly facing the direction from which the simulated load originates, is compressed against an adjacent portion of the modelled thread portion and central shaft.

Being so compressed, the stress concentration in the simulated bone tissue portions is only of a maximum of magnitude of 3.768 MPa, which has advantageously around 28% lower that of the buttress thread.

It is also shown that at the opposite side of the bone material adjacent the thread, that is the side not facing the direction from which the simulated load originates, a sufficient amount of stress is induced within the bone material but not negligible as is shown in FIG. 2A.

As will be understood and as clearly demonstrated by modelling the prior art screw thread provides (a) excessive stress adjacent bone on a first side of the screw device and (b) insufficient stress to adjacent bone on the opposed side of the screw device By contrast, the present invention (a) reduces excessive stresses on the first side of the screw device whilst (b) providing stresses in adjacent bone on the opposed side of the screw device thus reducing stress shielding.

Also as identified by the present inventors, traditional buttress threads as used in orthopaedic implants can often loosen easily, as such a thread is not designed specifically for human bone.

As such and as identified by the present inventors as a problem with the prior art and as recited above, with buttress thread design extremely high stress has been found by the present inventors which will concentrate on the weight bearing part of bone, while no stress occur at the opposite part of bone, both of which can cause bone loss and resorption around the screw.

As demonstrated in FIGS. 2A and 2B, the recess as provided by the present and crest features result in a more even distribution of load to adjacent bone tissue, obviating the identified problems with buttress threads of the prior art.

Figure 3A:
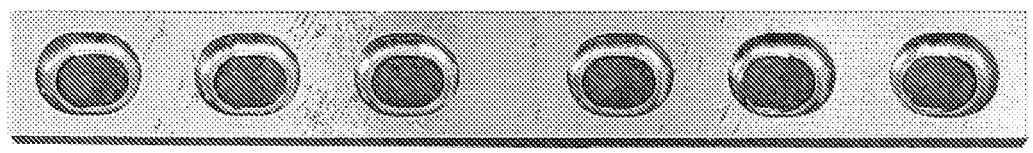
FIG. 3A shows a photographic representation of a dynamic compression plate utilised in the biomechanical test of the bone implant devices.
Figure 3B:
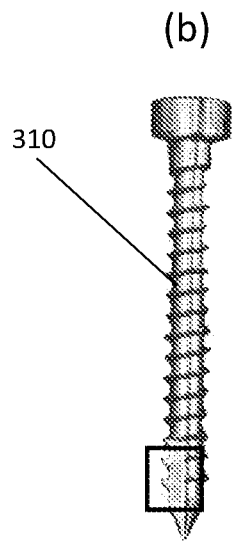
FIG. 3B shows a photographic representation of a bone screw of the prior art with a typical buttress thread.

Referring to FIG. 3B, there is illustrated a typical bone screw 310 of the Prior Art used for fixing fractured or fragmented bone so that fragmented or fractured bone may be reduced to their correct anatomical positions while osteosynthesis, or bone healing, takes place.

Bone screw 310 of the prior art includes a thread portion comprised of a helical thread having a buttress profile 315 that follows a helical path around the central path of the bone screw 310.

Figure 3C:
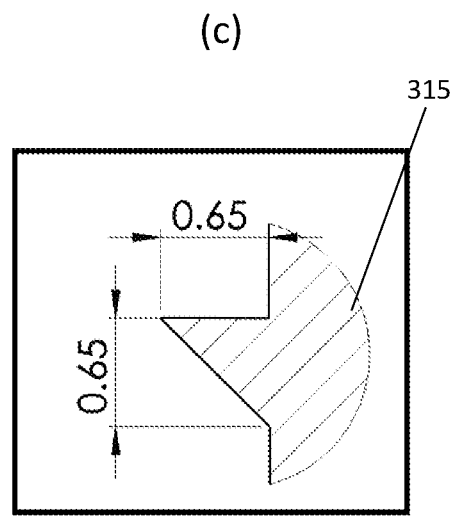
FIG. 3C refers to the thread profile of a typical buttress thread of the bone screw as shown in FIG. 3B.

The buttress profile 315 of the bone screw 310 is shown in FIG. 3C, wherein the thread portion of the buttress thread 315 includes a leading edge facing at least in a direction towards the distal end, a crest and a trailing edge faces at least in a direction of towards the proximal end. No undercut facet is included in the buttress thread profile 315 of the prior art.

Figure 3D:
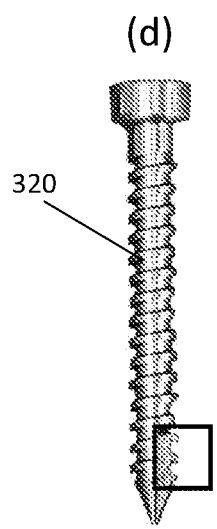
FIG. 3D shows a photographic representation of a bone screw according to the present invention, wherein the bone screw exhibits an undercut thread.
Figure 3E:
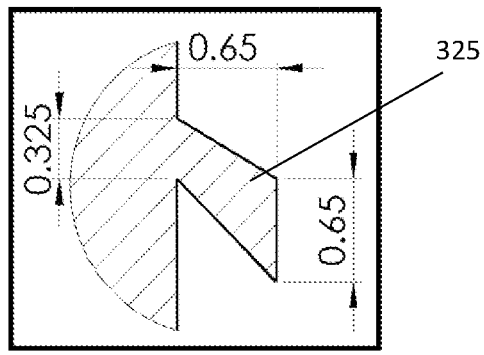
FIG. 3E refers to an exemplary embodiment of the thread profile of the undercut thread of the bone screw as shown in FIG. 3D.

FIG. 3D shows a photographic representation of an embodiment of the bone screw 320 according to the present invention. Same as that of the prior art, bone screw 220 includes a thread portion that follows a helical path around the central path of the bone screw 320. However, unlike bone screw 310 of the prior art, the bone screw 320 of the present invention includes an undercut thread profile 325 as is shown in FIG. 3E.

The undercut thread 325 of the present design is different from the buttress thread profile 315 of the prior art by having a leading edge facing at least in a direction towards the distal end, a flat top facet and an undercut structure as is illustrated in FIG. 1D.

Figure 4A:
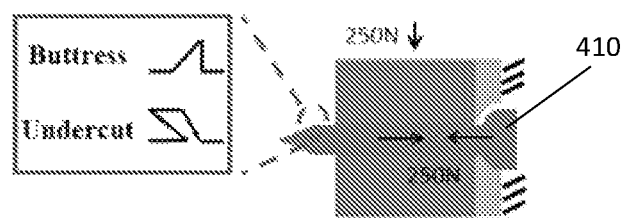
FIG. 4A shows a schematic representation of a bone screw with a typical buttress thread or an undercut thread according to the present invention being inserted into the bone material, with a load applied thereto.

Referring now to FIG. 4A, which illustrates the initial conditions, prior to loading, of the three-dimensional finite element analysis (FEA) model constructed utilising mechanical simulation software, used to simulate the stress applied to bone tissue adjacent to an orthopaedic implant such as the bone implant device 410.

In this illustration, biomechanical characteristics of bone implant devices with typical buttress thread are compared with devices with undercut thread of the present invention.

Figure 4B:
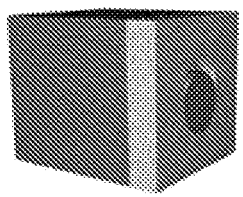
FIG. 4B illustrates a three-dimensional finite element analysis (FEA) model of a bone screw and its adjacent bone material, for assessment of load transfer characteristics to adjacent bone material.
Figure 4C:
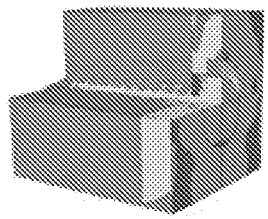
FIG. 4C shows an example of the finite element analysis (FEA) simulation results showing the stress applied to the bone material adjacent to the bone screw, in response to the application of load.
Figure 4D:
FIG. 4D shows an example of the finite element analysis (FEA) simulation results showing the stress applied to the bone screw in response to the application of load.

An example of the finite element analysis (FEA) simulation results showing the stress applied to the bone material adjacent to the bone screw is shown in FIG. 4C; and the stress within the bone screw is shown for example in FIG. 4D.

Figure 5A:
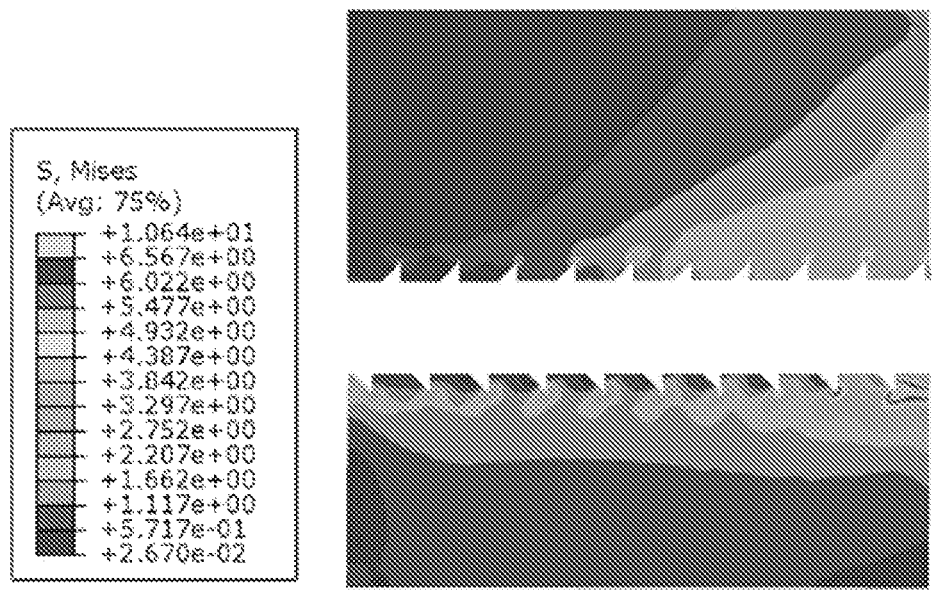
FIG. 5A is the finite element analysis (FEA) results showing the Von Mises stresses induced in the bone material adjacent the bone screw of FIG. 3B.

FIG. 5A shows the analysis results of the FEA model shown and described in reference to FIG. 4A and FIG. 4B, showing the Von Mises stresses induced in the bone material adjacent the bone screw with typical buttress thread, as shown in FIG. B As can be seen in FIG. 5A, being so urged by the load, the region of the simulated bone tissue, adjacent to the side of the implant is compressed against an adjacent portion of the modelled thread portion and central shaft.

Being so compressed, stress concentrations are shown with magnitudes in the simulated bone tissue portions, of a maximum of magnitude of 10.8 MPa.

In a clinical application, exposure of the real equivalent of the bone portions to high concentrations can lead to damage of the bone tissue in the form of undesirable mechanobiological effects such as the disruption of bone remodeling activity, necrosis and bone resorption.

Figure 5B:
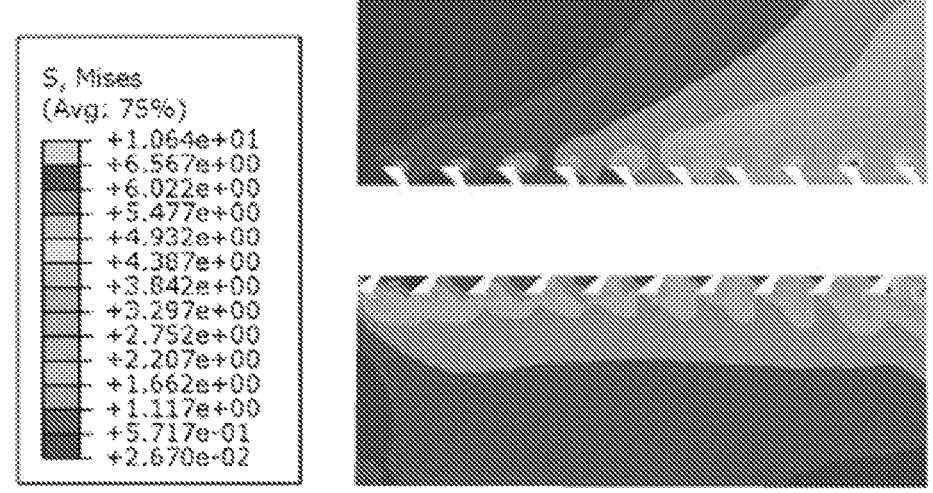
FIG. 5B is the finite element analysis (FEA) results showing the Von Mises stresses induced in the bone material adjacent the bone screw of FIG. 3D.

FIG. 5B illustrates the conditions following load of the model of the bone screw model with undercut thread as shown in FIG. 4A and FIG. B Similar to the result shown in FIG. 5A, being so urged by the load, the region of the simulated bone tissue, adjacent to the side of the implant is compressed against an adjacent portion of the modelled thread portion and central shaft.

However, it is noted that the stress concentration of the simulated bone tissue portions is only of a maximum of magnitude of 6.5 MPa, which is much lower than that of the results as shown in FIG. 5A.

It is also shown that in this model, the distribution of stress concentration at each thread is more even. Exposure of bone tissue to such an acceptable physiological range would maintain bone health through mechanobiological stimulation as in Wolff's Law, while being less than the magnitude necessary to cause damage to bone tissue.

In a clinical application, the distribution of stress to across the bone tissue surrounding both the side facing a load and the side opposite may have utility in providing firm fixation of orthopaedic implants in bone while stimulating bone health and strength.

Figures 5C, 5D:
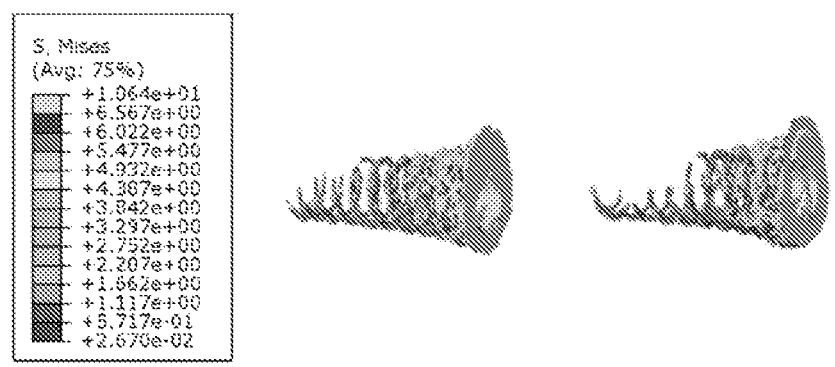
FIG. 5C is the finite element analysis (FEA) results showing the Von Mises stresses induced in the bone screw of FIG. 3B.
FIG. 5D is the finite element analysis (FEA) results showing the Von Mises stresses induced in the bone screw of FIG. 5D.

FIG. 5C illustrates the Von Mises stresses induced in the bone screw with buttress thread of FIG. 3B, while FIG. 5D shows the Von Mises stresses induced in the bone screw with undercut thread shown of FIG. 3D. As can be seen, the bone screw with undercut thread demonstrates a more even distribution of stress over the entire screw body than that of the buttress thread, and thus avoiding stress concentration at a specific point on the screw which may eventually lead to the local damage of the bone screws and even breakage thereof.

Figure 6A:
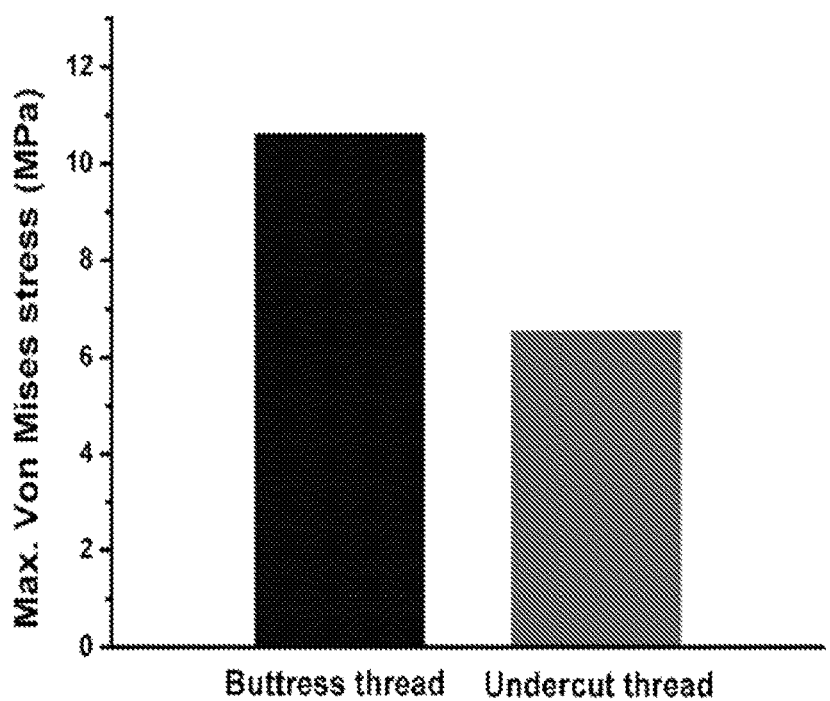
FIG. 6A is a bar chart showing the comparison of the maximum Von Mises stresses induced in the bone material adjacent the two bone screws shown of FIG. 3B and FIG. 3D.

FIG. 6A is a bar chart showing the comparison of the maximum Von Mises stresses induced in bone material adjacent the two bone screws shown of FIG. 3B and FIG. 3D. It is shown that with the use of the undercut thread of the present invention, the maximum Von Mises stress induced in the bone material adjacent to the bone screw is only around 6.5 MPa, which is around 38% lower than that induced by the typical buttress thread.

With the use of the bone screw of the prior art with the typical buttress thread, the maximum Von Mises stress induced in the bone material adjacent to the bone screw reaches 10.5 MPa.

Figure 6B:
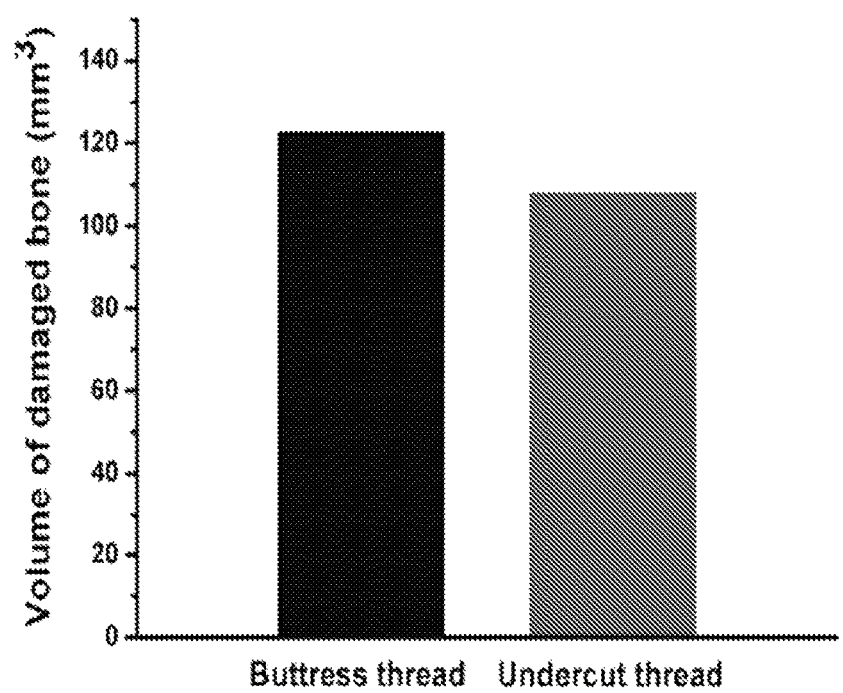
FIG. 6B is a bar chart showing the comparison of the bone volume damaged by the two bone screws shown of FIG. 3B and FIG. 3D.

FIG. 6B is a bar chart showing the comparison of the volume of damaged bone by the two bone screws shown of FIG. 3B and FIG. D The volume of damaged bone by the buttress thread is around 120 mm$^3$, while the volume of damaged bone by the undercut thread is only around 110 mm$^3$.

It is shown in the FEA results that the undercut thread of the bone screw of the present invention may induce less stress to the bone material adjacent to the cone screw, and thus imposing less damage to the bone.

FIG. 7A is a diagram showing an experimental setup for assessing the displacement of a comparison between two bone screws of the prior art and the present invention shown of FIG. 3B and FIG. 3D in response to a pulling force. Each screw is inserted into its own separate block of 10 g/cc polyurethane foam (Sawbones ASTM Type 10)

Each screw is then pulled away from its corresponding block at a displacement rate of 5 mm per minute, with the graphical representation as shown in FIG. 7B, via a pulling force applied on the proximal ends of the screws by a steel armature. Force was measured by a loadcell above the block.

In another biomechanical test, a pulling force is applied to the both screws of the prior art and that of the present invention shown of FIG. 3B and FIG. 3D. Such experimental set up is illustrated in FIG. 8A. In this test, each screw is inserted into its own separate block, with the hole directed normal to the surface.

Each screw is then pushed through its corresponding block with at a displacement rate of 5 mm per minute, with the graphical representation as shown in FIG. 8B, via a force applied by a hydraulic press applied evenly on both distal and proximal ends of the screws simultaneously by a steel armature. Force was measured by a loadcell below the block.

FIG. 9A shows a further experimental setup for applying a craniocaudal force to the two screws of the prior art and the present invention as shown of FIGS. 3B and 3D, and the displacement thereof in response to the applied force is recorded correspondingly.

In this biomechanical test, two screws of the same type are inserted into a single block, with the hole directed normal to the surface. The block is then pushed through in a direction perpendicular to the screws with a craniocaudal force which starts from 100-200N and increases 50N every 100 cycle. The graphical representation of the applied force control is shown in FIG. 9B.

Another biomechanical test is to apply a torsional force to the two screws shown of FIGS. 3B and 3D and the block. The experimental setup of which is illustrated in FIG. 10A. Similar to the test of FIG. 9A, two screws of the same type are inserted into a single block, with the hole directed normal to the surface.

A torque which starts from plus or minus 1 Nm and increases 0.1 Nm every 100 cycles is applied to the block by a steel armature. The graphical representation of the applied torque control is shown in FIG. 10B.

Figure 11:
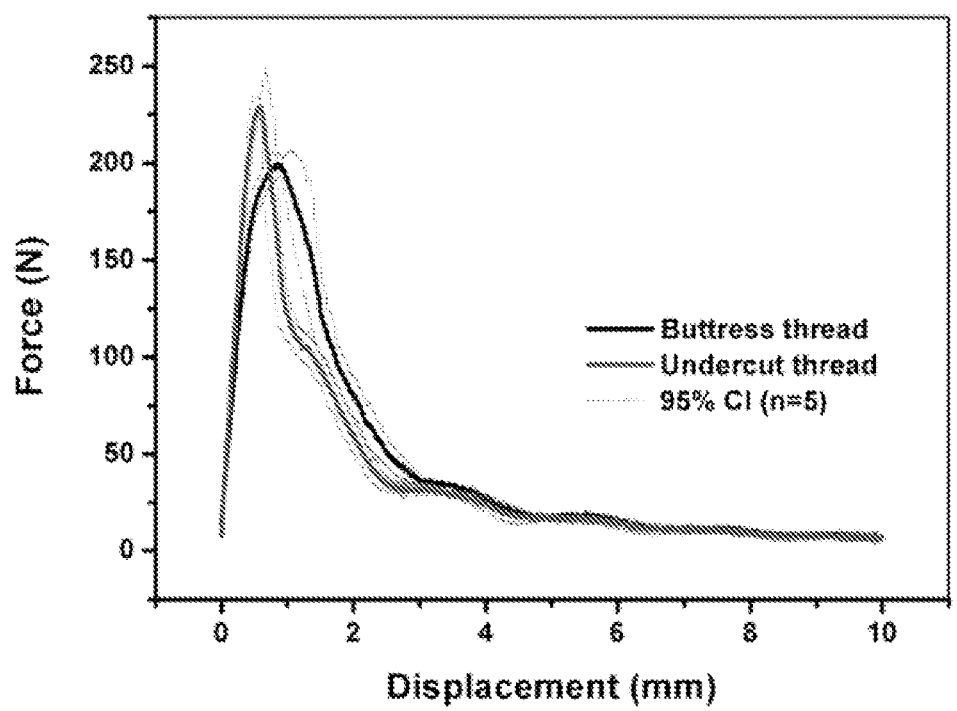
FIG. 11 is a graph of force versus displacement result of the displacement experiment described in FIG. 7A and FIG. 7B.

Referring to FIG. 11, there is shown a graph of force versus displacement when the two bone screws with buttress thread and undercut thread have a pull out force applied as is shown in FIG. 7A and FIG. 7B.

As can be seen, the bone screw with undercut thread has a lower displacement than that with the buttress thread when a force of the same magnitude is applied thereto. Comparing the slopes of the two curves before yield, the undercut thread has a steeper slope than the buttress thread, indicating that the bone screw with the undercut thread exhibits higher stiffness, and thus a higher resistance to deformation in resistance to an applied force.

Also as shown in FIG. 11, the undercut thread has a larger maximum yield than that of the buttress thread, as the maximum yield of the undercut thread is slightly higher than 225N while the maximum yield of the buttress thread is only around 200N. This shows that the undercut thread can withstand a larger stress until it reaches the limit beyond which the deformation switches from elastic to inelastic.

Figure 12:
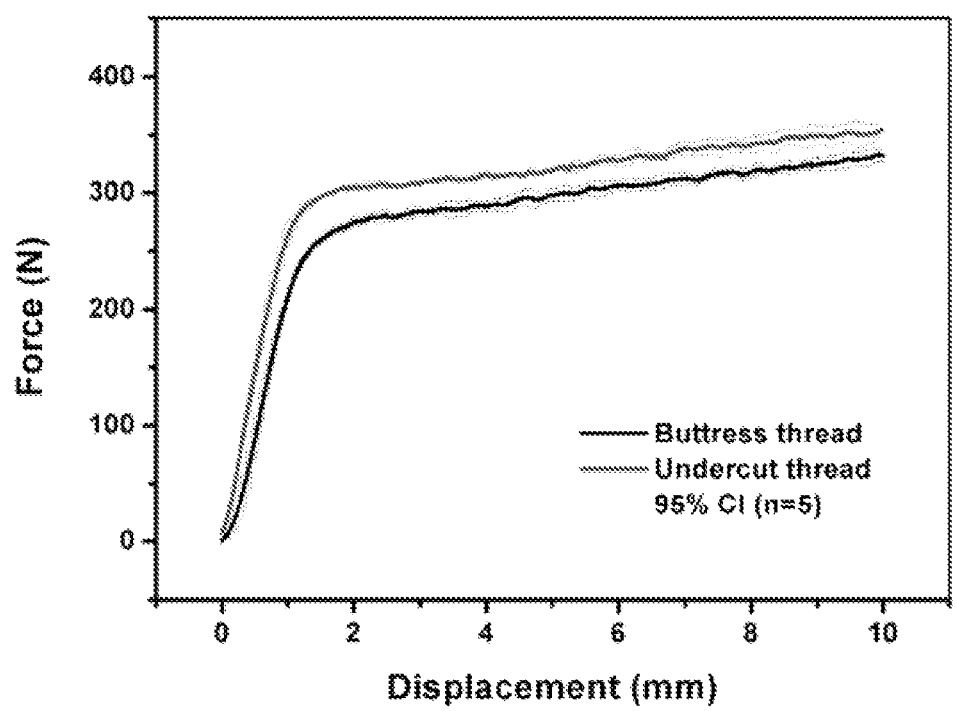
FIG. 12 is a graph of force versus displacement result of the displacement experiment described in FIG. 8A and FIG. 8B.

Referring now to FIG. 12, the displacement curves of the two bone screws with buttress thread and undercut thread in response to a pushing force are shown.

Again, it can be seen in the graph that undercut thread has a steeper slope than the buttress thread before yield, indicating that the bone screw with the undercut thread has a higher stiffness and thus a higher resistance to elastic deformation in response to a pushing force. The maximum yield of the undercut thread is also higher than that of the buttress thread, indicating that the undercut thread can withstand a larger stress until it reaches the limit beyond which the deformation switches from elastic to inelastic.

Figure 13A:
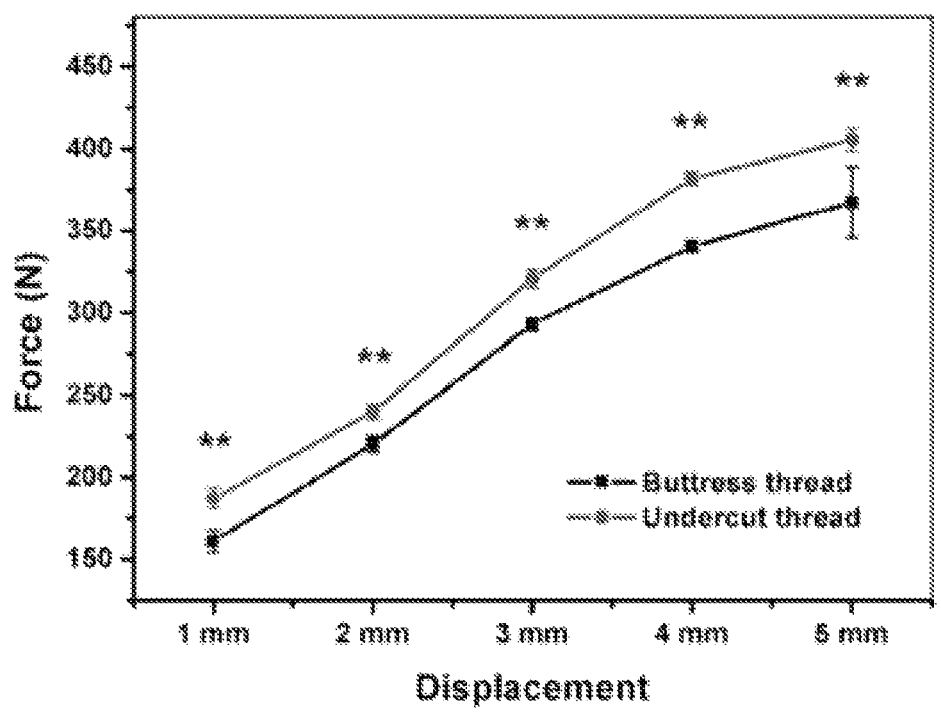
FIG. 13A is a graph of force versus displacement result of the displacement experiment described in FIG. 9A and FIG. 9B.
Figure 13B:
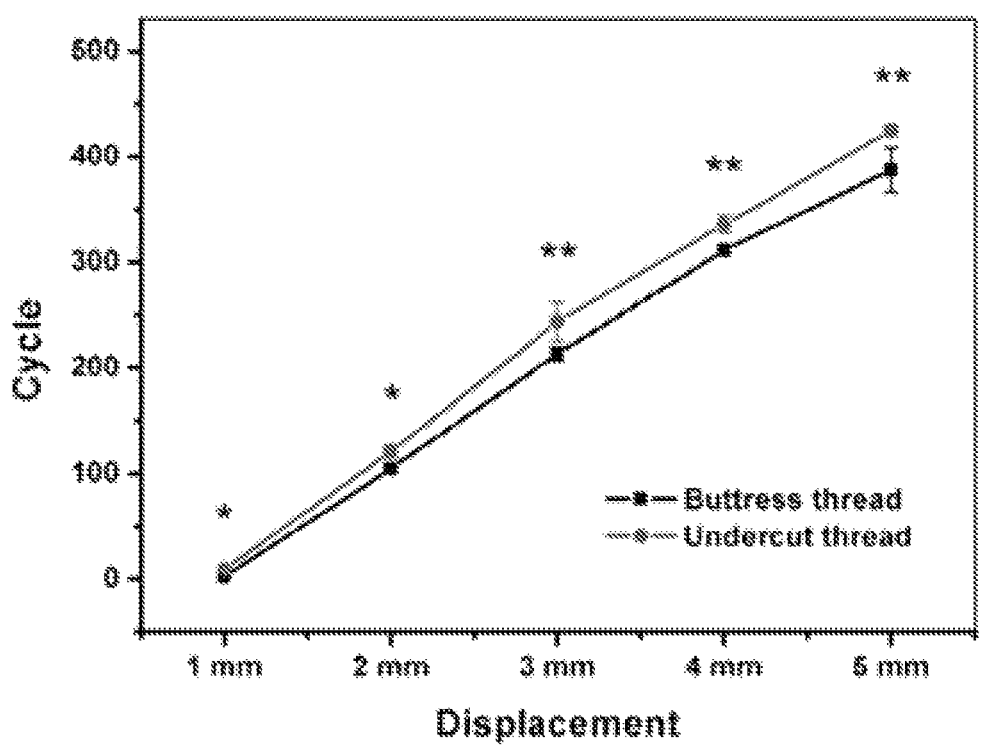
FIG. 13B is a graph of cycle versus displacement result of the displacement experiment described in FIG. 9A and FIG. 9B.

FIG. 13A and FIG. 13B shows a graphical representation of the results of the displacement experiment described in FIG. 9A and FIG. 9B, wherein a craniocaudal force starting from 100-200 N and increasing 50N every 100 cycles is applied to the blocks and the bone screws inserted thereto.

Referring to the force versus displacement graph of FIG. 13A, it is shown that the bone screw with the undercut thread has a lower displacement than that with the buttress thread when a force of the same magnitude is applied to the two screws. It is also shown in FIG. 13B that the undercut thread has a lower displacement than the buttress thread when they are at the same cycle. It is noted than when the number of force cycles increases, the difference in displacement between the two bone screws also increases.

Figure 14A:
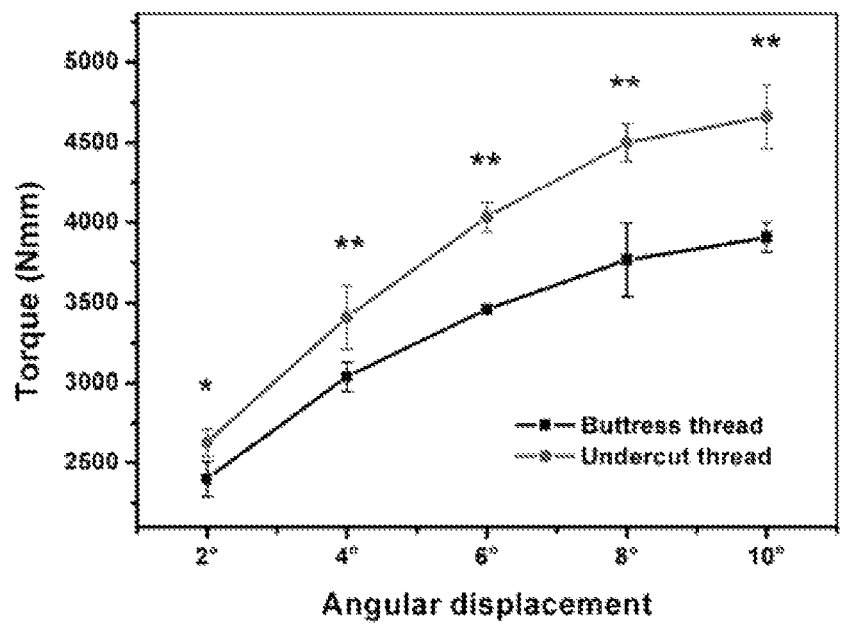
FIG. 14A is a graph of torque versus angular displacement result of the displacement experiment described in FIG. 10A and FIG. 10B.

FIG. 14A is a graph of torque versus angular displacement result of the displacement experiment described in FIG. 10A and FIG. 10B. As can be seen, a greater torque is required for the bone screw with the undercut thread to result in the same angular displacement. This shows that the undercut thread has a greater torsional stability than the buttress thread, and that the undercut thread exhibits a greater resistance to torque loading.

Figure 14B:
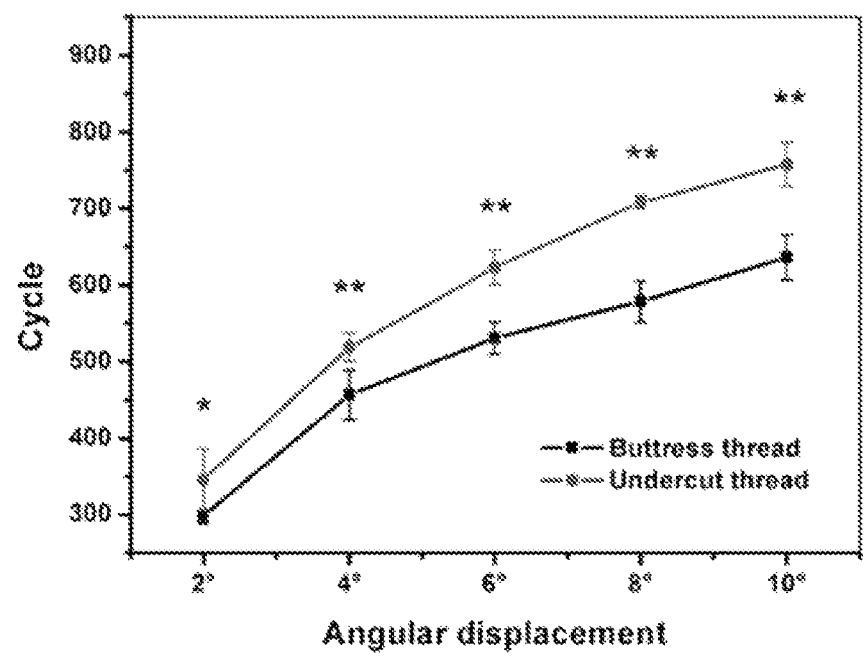
FIG. 14B is a graph of cycle versus angular displacement result of the displacement experiment described in FIG. 10A and FIG. B

Similarly as shown in FIG. 14B, the undercut thread shows a lower angular displacement when both screws are at the same cycle. The difference in angular displacement between the two screws increases when the number of cycles increases.

The invention claimed is:

1. An implant device for engagement with a bone of a subject, said implant device comprising a distal end, a proximal end, a central shaft extending therebetween and a longitudinal central axis;
   said implant device further including a helical thread portion extending circumferentially about said central shaft and extending in a direction from the distal end of the implant device and towards the proximal end thereof, and a root at the base of the helical thread portion adjacent the central shaft of the of the implant device, said helical thread portion in cross section including:
   a leading edge and a trailing edge, both of which extend at least radially outwardly from the central shaft and define the thread portion therebetween, whereby a root of the thread portion is defined therebetween in a direction of the longitudinal central axis of the implant device; and
   a crest portion disposed between the leading edge and the trailing edge and wherein said crest portion forms a radially outward portion of the thread portion, and wherein, the crest portion provides an engagement surface for abutment and engagement with bone of a subject radially disposed at said thread portion;
   wherein said leading edge faces in a direction at least towards the distal end of the implant device, and wherein said trailing edge faces at least in a direction towards the proximal end of the implant device;
   wherein a portion of the leading edge extends in a direction towards the distal end of the implant device further than the most distal portion of the root of the thread portion and wherein the distance in the longitudinal direction from the most proximal portion of the root to the most distal portion of the leading edge is greater than the longitudinal length of the root, such that said portion of the leading edge forms a recess between the central shaft and the leading edge;
   wherein the portion of said leading edge defining said recess between the central shaft and the leading edge provides for abutment and engagement with bone tissue of a subject disposed within said recess;
   wherein the trailing edge extends in a direction of from the most proximal portion of the root in a radial outward direction towards the distal end;
   wherein the leading edge of the thread portion includes a first facet and a second facet for abutment and engagement with bone tissue of a subject, the first facet has a substantially planar surface and extends substantially radially outwardly from the distal side of the root portion at the central shaft towards the crest portion; and
   wherein the second facet has a substantially planar surface and is disposed between the root of the thread portion and the first facet, and extends radially outwardly from the shaft substantially normal to the longitudinal central axis of the implant device towards the first facet.

2. An implant device according to claim 1, wherein the crest portion has a surface which is substantially planar and parallel with the longitudinal central axis of the implant device which provides said engagement surface.

3. An implant device according to claim 1, wherein the crest portion forms at least a portion of the trailing edge.

4. An implant device according to claim 1, wherein said recess formed by the leading edge is sized and shaped, such that upon engagement with radially disposed bone adjacent the thread portion, provides for distribution of stress induced in said bone adjacent the leading edge and provides for reducing stress concentration in bone adjacent said leading edge.

5. An implant device according to claim 1, wherein the first facet extends substantially radially outwardly from the distal side of the root at the central shaft towards the crest portion at an inclination angle in the range of from 95 degrees and 150 degrees subtended between said planar surface and the longitudinal central axis.

6. An implant device according to claim 5, wherein said inclination angle is in a range of from 100 degrees and 130 degrees subtended between said planar surface and the longitudinal central axis.

7. An implant device according to claim 5, wherein said inclination angle is about 120 degrees subtended between said planar surface and the longitudinal central axis.

8. An implant device according of claim 1, and wherein the trailing edge of thread portion includes a third facet for abutment and engagement with bone tissue of a subject, wherein the third facet is substantially planar and extends from the proximal side of the root at the central shaft and extends towards the crest portion at an inclination to the central shaft.

9. An implant device according to claim 1, wherein the engagement surface of the crest portion is at least partially provided by the leading edge.

10. An implant device according to claim 1, wherein the engagement surface of the crest portion is at least partially provided by the trailing edge.

11. An implant device for engagement with a bone of a subject, said implant device comprising a distal end, a proximal end, a central shaft extending therebetween and a longitudinal central axis;
    said implant device further including a helical thread portion extending circumferentially about said central shaft and extending in a direction from the distal end of the implant device and towards the proximal end thereof, and a root at the base of the helical thread portion adjacent the central shaft of the of the implant device, said helical thread portion in cross section including:
    a leading edge and a trailing edge, both of which extend at least radially outwardly from the central shaft and define the thread portion therebetween, whereby a root of the thread portion is defined therebetween in a direction of the longitudinal central axis of the implant device;

a crest portion disposed between the leading edge and the trailing edge and wherein said crest portion forms a radially outward portion of the thread portion, and wherein, the crest portion provides an engagement surface for abutment and engagement with bone of a subject radially disposed at said thread portion, the crest portion has a greater longitudinal length than that of the root in the direction of the longitudinal central axis of the implant device;

wherein said leading edge faces in a direction at least towards the distal end of the implant device, and wherein said trailing edge faces at least in a direction towards the proximal end of the implant device;

wherein a portion of the leading edge extends in a direction towards the distal end of the implant device further than the most distal portion of the root of the thread portion and wherein the distance in the longitudinal direction from the most proximal portion of the root to the most distal portion of the leading edge is greater than the longitudinal length of the root, such that said portion of the leading edge forms a recess between the central shaft and the leading edge; wherein the portion of said leading edge defining said recess between the central shaft and the leading edge provides for abutment and engagement with bone tissue of a subject disposed within said recess; and wherein the trailing edge extends in a direction of from the most proximal portion of the root in a radial outward direction towards the distal end.

12. A bone screw comprising:
a. a screw shaft;
b. a screw head;
c. a screw tip;
d. a thread; and
e. an undercut structure in the thread facing the screw tip,
wherein the thread comprises a thread surface facing the screw head having an angle larger than 90 degrees with the screw shaft, and wherein the undercut structure is formed in a leading edge of the thread that has first and second facets, said second facet extending from the screw shaft substantially normal to a longitudinal central axis thereof and said first facet extending from an end of the second facet at an inclination angle in the range of 95 degrees and 150 degrees to a crest surface parallel to the longitudinal central axis.

13. The bone screw according to claim 12 further comprising a flat thread edge of the thread.

\* \* \* \* \*